United States Patent [19]

Dale et al.

[11] 4,028,342

[45] June 7, 1977

[54] POLYMERIC PHENOLIC ANTIOXIDANTS

[75] Inventors: James A. Dale, Menlo Park; William J. Leonard, San Francisco, both of Calif.

[73] Assignee: Dynapol Corporation, Palo Alto, Calif.

[22] Filed: May 29, 1975

[21] Appl. No.: 581,611

Related U.S. Application Data

[62] Division of Ser. No. 449,929, March 11, 1974, Pat. No. 3,930,047.

[52] U.S. Cl. .................. 260/47 UA; 260/619 R; 260/619 D; 426/546
[51] Int. Cl.² ................. A23D 5/04; C08F 19/10
[58] Field of Search ....... 260/47 UA, 619 R, 619 D

[56] References Cited

UNITED STATES PATENTS

| | | | |
|---|---|---|---|
| 2,450,766 | 5/1947 | Nixon et al. | 260/624 |
| 3,004,953 | 10/1961 | Sonnabend | 260/62 |
| 3,075,832 | 1/1963 | Ecke | 260/619 D |
| 3,645,970 | 2/1972 | Kleiner | 260/47 UA |
| 3,758,597 | 9/1973 | Buysch et al. | 260/619 D |
| 3,930,047 | 12/1975 | Dale et al. | 426/546 |

FOREIGN PATENTS OR APPLICATIONS

| | | | |
|---|---|---|---|
| 165,884 | 4/1954 | Australia | |
| 709,865 | 5/1965 | Canada | 260/619 R |

*Primary Examiner*—Joseph L. Schofer
*Assistant Examiner*—Peter F. Kulkosky
*Attorney, Agent, or Firm*—William H. Benz

[57] ABSTRACT

Polymeric phenols of the formula

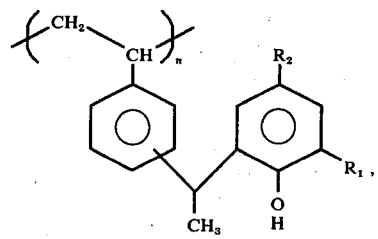

wherein $n$ is an integer from 3 to 2,000, $R_1$ is a lower alkyl and $R_2$ is hydrogen or a lower alkyl, are disclosed. Their preparation and preferred use as antioxidants, especially nonabsorbable food antioxidants, are also disclosed.

14 Claims, No Drawings

POLYMERIC PHENOLIC ANTIOXIDANTS

This is a division of application Ser. No. 449,929, filed Mar. 11, 1974 and now U.S. Pat. No. 3,930,047 issued on Dec. 30, 1976.

BACKGROUND OF THE INVENTION

1. Field of the Invention

This invention relates to polymeric antioxidants. In particular, it relates to novel polymeric phenolic antioxidants and their preparation.

2. The Prior Art

Phenolic compounds are known to be useful as antioxidants, stabilizing substrates such as petroleum products, resins, rubber, and in certain instances, foodstuffs. To find successful application as a foodstuff antioxidant, a phenolic material must be nontoxic, in addition to providing protection against oxidation.

Several phenolics have been used as antioxidants in foodstuffs, including butylated hydroxytoluene (BHT) and butylated hydroxyanisole (BHA). These compounds have not been wholly satisfactory for a variety of reasons. They are high in cost and lack sufficient "carry through"; that is, their inhibitory action is not carried through into finished food products, as for example, into baked goods, to a desired degree. Furthermore, toxicity questions have been raised which are serious enough to result in BHT and BHA's use being restricted in the United States and prohibited in some European countries.

Finding safe alternatives is difficult. When any phenolic is ingested and absorbed from the gastrointestinal tract into the body, toxicity problems are raised, since many phenolic derivatives are toxic and the exact products of phenolic metabolism are not well known or fully predictable.

These problems are overcome, however, when an antioxidant is employed which has a molecular size which prevents its being absorbed through the walls of the gastrointestinal tract. It is such an antioxidant and its preparation to which this invention relates — a polymeric antioxidant which may be easily varied in molecular size to achieve the desired nonabsorption through the walls of the gastrointestinal tract. The antioxidants of this invention also find use in non-food applications, where their high molecular weight leads to low volatility and improved carry-through properties.

STATEMENT OF THE INVENTION

A new class of polymeric phenolic materials has now been discovered. These materials are of a molecular size so as to not appreciably be absorbed from the gastrointestinal tract. They exhibit substantial activity as antioxidants for fats, oils and other foodstuffs.

The polymeric phenolic materials of this invention are defined by the formula I,

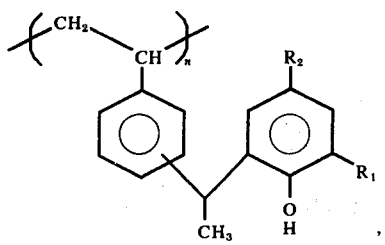

(I)

wherein $R_1$ is a lower alkyl of from 1 to 5 carbon atoms, $R_2$ is hydrogen or lower alkyl of from 1 to 5 carbon atoms, and $n$ is an integer of from about 3 to about 2,000.

These materials are homopolymers of α-(2-hydroxy-3,5-di-lower alkylphenyl)ethylvinylbenzene or α-(2-hydroxy-3-lower alkylphenyl)ethylvinylbenzene. Copolymers of these materials with vinyl-unsaturated materials may also be prepared.

These antioxidants are prepared by polymerizing the vinyl groups of α-(2-hydroxy-3-lower alkylphenyl)ethylvinylbenzene or α-(2-hydroxy-3,5-di-lower alkylphenyl)ethylvinylbenzene either cationically or, after blocking the hydroxyl groups, free radically. The free radically-polymerized material is then treated to unblock (restore) the phenol hydroxyl groups.

The monomeric phenolic precursor has a formula

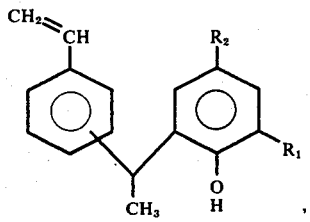

DETAILED DESCRIPTION OF THE INVENTION wherein $R_1$ and $R_2$ are as hereinabove set forth, and is thought to represent a new material as well.

The compounds in accord with this invention may be described as polyphenols or as polysytrylphenols because of their polystyrene-like linkage.

The terms "phenol", "phenols", or "phenolics" are used in their generally accepted sense and refer to a 1-hydroxybenzene structure. The phenolic materials of this invention have a saturated lower alkyl substituent attached to the phenol ring ortho to the hydroxyl group. This substituent is referred to as $R_1$ in the structural formula. Optionally and preferably, a second saturated lower alkyl substituent is attached to the phenolic ring at the 4 position, i.e., para to the hydroxy group. This substituent is referred to as $R_2$ in the structural formula. $R_1$ has from 1 to 5 carbon atoms and may be linear or branched. Thus $R_1$ may include, for example, methyl, ethyl, isopropyl, tertiary butyl, n-pentyl, α-methylbutyl, and the like. Generally, it is preferred to employ methyl, ethyl, or branched lower alkyls having 4 to 5 carbon atoms as $R_1$. The methyl and tertiary butyl are most preferred $R_1$ substituents. $R_2$ may be hydrogen or a lower alkyl of from 1 to 5 carbon atoms. Preferred $R_2$ groups are hydrogen, methyl, ethyl, and tertiary butyl, with methyl and tertiary butyl being most preferred.

The polymeric antioxidants of this invention comprise a plurality (3 to about 2,000) of

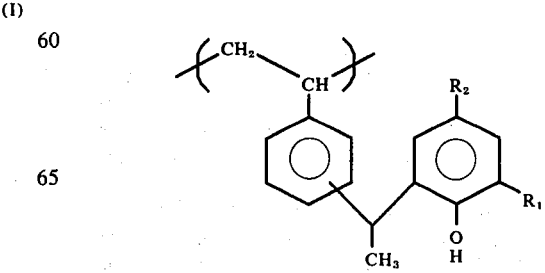

links. In a variation, vinyl group-containing monomers are copolymerized with these styryl links. These polymers may be formed by polymerizing or copolymerizing an olefinically unsaturated phenol or "styrylphenol" having the general structure

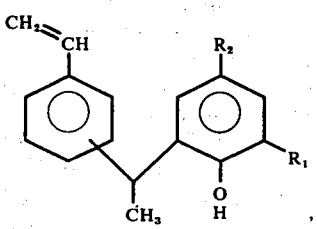

wherein $R_1$ and $R_2$ are as set forth above.

These olefinically unsaturated phenols are suitably prepared by reacting an $R_1$ and $R_2$-containing phenol (that is, a 2-alkylphenol or a 2,4-dialkylphenol) with divinylbenzene under alkylation conditions in the presence of a metal ion phenoxide phenol alkylation catalyst selected from the group consisting of aluminum$^{III}$ phenoxide, zirconium$^{IV}$ phenoxide, hafnium$^{IV}$ phenoxide, tantalum$^V$ phenoxide, and gallium$^{III}$ phenoxide. The alkylation catalyst is preferably aluminum$^{III}$ phenoxide. The catalyst may be added as the phenoxide or may be formed in situ in the reaction zone by reacting the metals themselves or their salts or other reactive compounds such as alkoxides and the like with an excess of the 2- or 2,4-alkylphenol. The amount of catalyst employed in the alkylation will vary between about 0.01% and about 25%, basis weight of alkylphenol compound. Generally, from about 0.1% to about 15% of alkylation catalyst (on the same weight basis) is preferred. The reaction is carried out in liquid phase, either using the reactants as solvent or, more commonly, using a suitable reaction solvent inert to the catalyst and the alkylation conditions. Typical solvents include saturated hydrocarbons such as cyclohexane and aromatics such as toluene, benzene or xylene. Ethers such as dioxane or diglyme also may be used. The reaction is carried out at elevated temperatures such as from about 75° C to about 300° C and in laboratory preparations most commonly atmospheric pressure. For commercial scale production, elevated reaction pressures, such as from 1 atmosphere to about 20 atmospheres may be employed. As a general rule, it is desirable to react at least one mole of divinylbenzene for each mole of alkylphenol. This molar ratio may range as high as up to 5 moles of divinylbenzene for each mole of alkylphenol. Reaction times depend upon the temperature and the exact reactants employed and can vary from a few minutes (such as 10 minutes) to several hours (such as 20 hours).

The 2-alkylphenol and 2,4-diakylphenol starting materials are commonly available. It should be noted, however, that they are not always readily available in absolutely isomerically pure form. Thus, it is clearly within the purview of this invention, even in its most preferred embodiments, to unintentionally employ in the polymeric materials minor amounts, say up to about 5%, of phenols which do not have the structures here-described. So, too, the divinylbenzene employed in the preparation of the phenolic monomer may be a mixture of isomers.

The styrylphenols may be polymerized in the presence of cationic or free radical initiators, or by other methods for "olefin"-type polymerization known in the art. Under certain conditions it is possible to polymerize styryl phenols directly; in certain instances it is necessary to block the phenol hydroxyl group prior to polymerization. This blocking may be carried out by derivatizing the hydroxyl, such as by acetylating or benzoylating the hydroxyl groups. These blockinge remain intact through the polymerization step and may be easily removed thereafter; for example, in the case of an ester blockage, by simple hydrolysis.

The cationic polymerizations are generally carried out without blocking the hydroxyl functionality. In a typical polymerization, the styryl monomer, dissolved in an ether, halohydrocarbon, or other inert solvent, is contacted with a catalytically effective amount of an acid catalyst such as sulfuric acid, boron trifluoride, or stannic chloride. This cationic polymerization is generally carried out at low temperatures such as from $-100°$ C to about 25° C. The amount of catalyst can range from about 0.01 to about 10%, basis weight of monomer. The reaction can take from about one hour to about 75 hours, with shorter times being preferred for commercial operations. The products of cationic polymerization as a rule tend to be somewhat smaller in molecular size than the products of free radical polymerization. Cationic polymerization is well suited for preparing materials defined by formula I, having values for $n$ of from 3 to 100, especially 3 to 50.

The free radical polymerizations generally are carried out with blocking of the phenol hydroxyl functionality. In a typical polymerization, the styryl monomer, dissolved in ether, aromatic hydrocarbon, or other inert solvent, is contacted with a catalytically effective amount (0.01% to about 5%, basis monomer) of a free radical initiator such as benzoyl peroxide di-tertbutyl-peroxide or azo-bis-isobutyronitrile (AIBN) at a moderately elevated temperature, such as from about 50° to about 125° C, for a period of from about one hour up to about 40 hours. The products of free radical polymerization tend on the average to be larger than the cationic products, generally having values for $n$ in formula I of from 100 to 2,000, especially 500 to 1,500.

The styrylphenols which find utility as precursors for the polymeric materials of this invention themselves have antioxidant properties in their monomeric form. The polymeric styrylphenol antioxidants contain $n$ styrylphenol units. $n$ may range in value from about 3 to about 2,000. Unless laborious fractionations are performed, a range of materials having a variety of molecular size will regularly be employed. The polymeric antioxidants of this invention find application in industrial materials and may be used to prevent or retard oxidation in synthetic rubber, fibers, lubricants, plastics, and the like. They find preferred application as antioxidants for foodstuffs, and feeds for man and animals, especially preventing rancidity of fats and oils and deterioration of food values such as flavors, fragrances or vitamins. In food applications it is preferred to employ these polymeric materials at molecular sizes which subtantially prevent their passage through the walls of the gastrointestinal tract, so as to avoid any possibility of toxicity with these materials.

Although molecule passage through the gastrointestinal tract walls is a multifaceted procedure depending upon the exact chemical composition of the molecule in question, generally, passage of these anitoxidants is substantially prevented (say, less than 5% of the amount ingested is absorbed through the gastrointestinal tract) when n is greater than about 10. A preferred range for n in food applications is between 20 and 1,500, with values from 40 to 1,250 being most preferred in food application.

These polymeric antioxidants are relatively hydrophobic in homopolymeric form. This makes their application with oils and fats very good, but limits their use in water or other polar media. This limitation may be avoided by emulsification or copolymerizing hydrophilic materials into the polymer product. Suitable comonomers for this purpose include vinyl group-condensing comonomers; for example, acrylic acid, methacrylic acid, acrylate and methacrylate esters, maleic anhydride, maleic acid, N-vinylpyrollidone and vinyl methyl ether. Styrene and other copolymerizable materials may be added. The copolymerizable groups may be present in the polymer in amounts of up to 2 moles (especially up to 1 mole) of comonomer per mole of monomeric styrylphenol. It is very suitable to add these copolymerizable materials to the polymerization mixture when the polymer is being formed.

In use, the antioxidants of this invention are admixed with the substrate being stabilized against oxidation. A stabilizing amount of these antioxidants is used. By a "stabilizing amount" is meant the amount which upon admixture is sufficient to stabilize the food or other substrate against oxidative deterioration. This amount will of course vary with the particular antioxidant and substrate employed. In general, however, only very small amounts of these antioxidants are employed, such that a stabilized composition will comprise substrate, such as foodstuff or a polymer, and from about 0.001% by weight of antioxidant (basis substrate) to about 1% by weight of antioxidant. Preferably, and especially in food applications, the antioxidant will be present in an amount of from 0.001% by weight to about 0.2% by weight of the substrate.

The antioxidants of this invention and their preparation will be further described by the following Examples, which are intended to illustrate the invention and are not to be construed as limiting its scope.

EXAMPLE I

A. A mixture of 4.3 g of 2,4-dimethylphenol and 2.04 g of aluminum isopropoxide are heated in a flask at 130° for 1 hour. Vacuum is applied for 0.5 hours to remove isopropanol. Then 70 ml of dried toluene is added as a reaction solvent, and the mixture is refluxed. A mixture of 5.2 g of divinylbenzene in 5 ml of toluene is then added, and the refluxing is continued for 2 hours. The reaction mixture is worked up by adding it to 300 ml of ether and extracting the resulting mixture twice with 2N HCL, twice with 2N NaOH, washing with a saturated NaCl solution, and drying ove MgSO₄. Solvent is stripped to yield 8.1 g of a crude oil product. The oil product is evaporated under vacuum to remove unreacted divinylbenzene and light impurities. The residue is column chromatographed to yield 2.3 g of pure α-(2-hydroxy-3,5-dimethylphenyl)ethylvinylbenzene monomer,

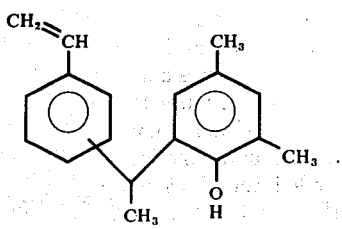

B. The monomer of part A is dissolved in 50 ml of diethyl ether containing 10.1 g of triethylamine, and chilled to 0° C. A mixture of 10.2 g of acetic anhydride in 20 ml of ether is added dropwise with stirring. The mixture is allowed to warm to room temperature and is stirred for one hour. Excess triethylamine and acetic anhydride is removed under vacuum. The residue is dissolved in 150 ml of ether; extracted with dilute HCl and dilute NaOH; washed with saturated NaCl; and dried. The product is distilled to yield 1.9 g of acetylated product.

C. A 1.5 g portion of the product of part B is combined with 4.2 mg of AIBN free radical initiator and 6 ml of benzene and heated at 70° C for 15 hours. More AIBN is added, and heating is continued for 22 more hours. The resulting product is precipitated as a white solid by adding the reaction mixture to methanol. The product is separated and dried. A 1 g portion of the dried product is dissolved in 50 ml of dioxane and 20 ml of tetrahydrofuran. 9 Milliliters of 1N NaOH is added and the solution becomes cloudy. The solution is then heated to reflux for 3 hours. The resulting product is extracted into chloroform after adding excess water; the chloroform layer is separated, washed with saturated aqueous NaCl, dried with Na₂SO₄, filtered, reduced under vacuum, and added slowly with stirring to methanol to precipitate 0.85 g. of fluffy solid. The product has a molecular weight, as determined by gel permeation chromatography comparison to polystyrenes, of 120,000 and a structure of

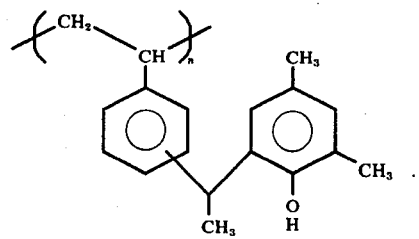

D. When the product of part C is added to animal fat-based cooking oils and the mixture is heated to 100° C in the presence of oxygen, the rate of oxidation of the oil is substantially reduced over the rate of oil alone exposed to the same heating in the presence of oxygen. When an antioxidant product made in accord with this example, but containing a radioactive carbon[14] tracer is fed to rats, it is noted that all the radioactivity is excreted with the rats' feces and none appears in the urine, indicating that the antioxidant is not absorbed from the gastrointestinal tract.

EXAMPLE II

A mixture of 1.08 g of orthocresol, about 20 ml of toluene, and a small amount of aluminum isopropoxide is heated to boiling and there maintained for one hour, 1.3 Grams of an 80% divinylbenzene is then added. The mixture is maintained at reflux for 20 hours. The product is worked up and column chromatographed in accord with the procedures of part A of Example I to yield

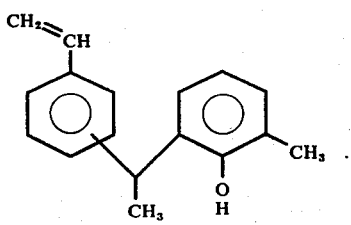

This material is acetylated in accord with the procedures of part B of Example I and then polymerized by the general method of part C of Example I to yield, after hydrolysis, the polymeric antioxidant,

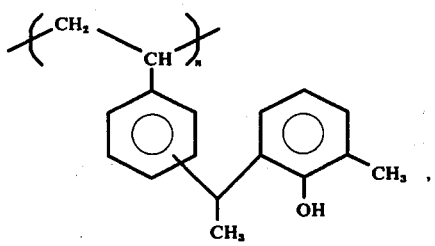

having a molecular weight, as determined by gel permeation chromatography comparison with polystyrene, of 25,000.

When tested by the methods of part D of Example I, the material is observed to exhibit antioxidant activity and to be nonabsorbable.

EXAMPLE III

The monomer preparation of part a of Example I is repeated. 50 Milligrams of the product is dissolved in 2 ml of distilled dichloromethane and cooled in a Dry-Ice/-propanol bath. Two microliters of $BF_3$.etherate is added and the mixture is stirred in the bath for 2 hours; then at room temperature for 15 hours. Thin layer chromatography indicates that although substantial polymerization has occurred, monomer remains. An additional 2 microliters of $BF_3$.etherate is added, and the mixture is stirred at room temperature for 2 days. The reaction mixture is worked up.

It is diluted with ether,
extracted with saturated $Na_2CO_3$,
washed with saturate NaCl,
dried over $MgSO_4$, and filtered.
Solvent is then stripped off under vacuum.

Gel permeation analysis of the product shows that it has an average molecular weight of 3,800. This product, like the products of Example I and II, would be a nonabsorbable antioxidant.

EXAMPLE IV

The polymerization experiment of Example III is repeated with several changes: 100 mg of product monomer is used,; 4 microliters of catalyst is used directly; and only 1 ml of dichloromethane is used. The mixture is maintained in the dry ice bath for three days and then is left at room temperature for 2 days. The final product, after recovery, has a molecular weight, by gel permeation chromatography, of 12,000.

EXAMPLE V

The experiment of Example I is repeated with two changes. Instead of 2,4-dimethylphenol, 2-methyl-4-ethylphenol is employed as starting material.

The product recovered in part A is α-(2-hydroxy-3-methyl-5-ethylphenyl)ethylvinylbenzene monomer,

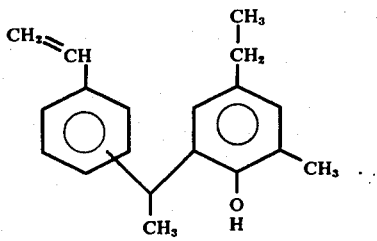

The polymerization of step C is carried out in the presence of 8 mg of AIBN free radical initiator and continued for about 14 hours. The final product has a molecular weight, by gel permeation chromatography, of about 50,000, and a structure of

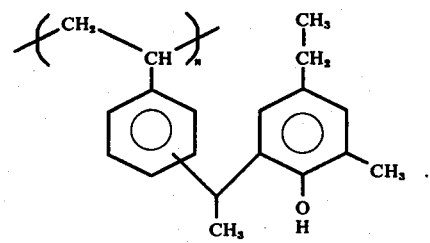

EXAMPLES VI – IX

The monomer preparation of part A of Example I is repeated 4 times, varying the metal alkylation catalyst employed.

VI

Instead of 2.04 g of aluminum isopropoxide, 1.2 g of gallium isopropoxide is employed as catalyst. The same generation of phenoxide, in this case, gallium 2,4-dimethyl phenoxide, and removal of isopropanol is used, as is the same product workup. A similar yield of the same α-(2-hydroxy-3,5-dimethylphenyl)ethylvinylbenzene is achieved, which can be employed in accordance with parts B, C and D of Example I.

VII

Instead of 2.04 g of aluminum isopropoxide, 0.36 g of tantalum pentachloride in 0.2 ml of benzene is employed as catalyst. After removing the benzene by vaporization, the mixture is refluxed overnight to form the tantalum 2,4-dimethylphenoxide catalyst. Toluene and divinylbenzene are added and the alkylation carried out. After a workup in accordance with part A of Example I, a similar yield of the same styrylphenol product is obtained.

VIII

Instead of aluminum isopropoxide, 0.8 g of tetrabutyl zirconate (as a 30% solution in xylene) is added to the 2,4-dimethylphenol. Butyl alcohol and xylene are removed with heat and vacuum to yield zirconium 2,4-dimethylphenoxide, which upon addition of toluene and divinylbenzene and reaction in accordance with part A of Example I, functions as an alkylation catalyst, yielding a similar yield of the same styryl monomer.

IX

Hafnium oxychloride (HfOCl$_2$.8H$_2$O) is prepared by the method of Bradley et al, J. Chem. Soc., 1953, pp. 1634–6.

0.5 Grams of the oxychloride is added to 4.3 g of 2,4-dimethylphenol and refluxed with stirring until no more water is produced (48 hours), and a hafnium 2,4-dimethylphenoxide is prepared. Toluene and divinylbenzene are then added, and the procedures of Example I are repeated. After workup, a similar yield to Example I's of the styrylphenol of Example I is recovered.

EXAMPLE X

A. A solution of 120 mg of the acetylated monomeric styrylphenol of part B of Example I, 49 mg of sublimed maleic anhydride, and 0.4 mg of AIBN (recrystallized from chloroform) in 0.5 ml of THF is purged with argon for 10 minutes, capped and heated at 70° C for 20 hours. The product mixture is dropped into 30 ml of cooled (0° C) methanol to yield 90 mg of white powder, which is collected, washed and dried, and determined to be a copolymer of maleic anhydride and the acetylated styryl monomer.

B. 35 Milligrams of the product of part A is added to 10 ml of 1N sodium hydroxide and refluxed with stirring under argon. The reaction mixture is cooled and acidified to pH2 with hydrochloric acid. A precipitate appears which is extracted into ethyl acetate.

EXAMPLE XI

The procedure of Example X is repeated, using the acetylated cresol-based monomer of Example II as styryl phenol monomer. A copolymer of maleic acid and α-(2-hydroxy-3-methylphenyl)ethylvinylbenzene results.

We claim

1. A material consisting essentially of a compound having the structural formula

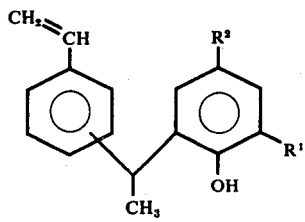

wherein R$_1$ is a lower alkyl of from 1 to 5 carbons inclusive, and R$_2$ is hydrogen.

2. The compound of claim 1, wherein R$_1$ is a methyl group.

3. A polymer comprising n units of a monomer of the formula

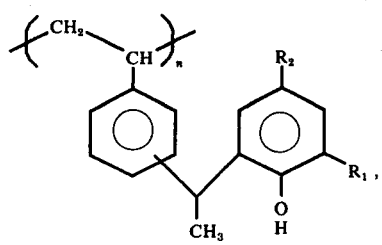

wherein R$_1$ is a lower alkyl of from 1 to 5 carbons inclusive, R$_2$ is hydrogen or a lower alkyl of from 1 to 5 carbons, and n is from 3 to 2,000.

4. The polymer of claim 3, wherein R$_1$ is methyl, and n is from 20 to 1,500.

5. The polymer of claim 4, wherein R$_2$ is methyl or hydrogen.

6. The polymer of claim 3, consisting essentially of n units of the formula

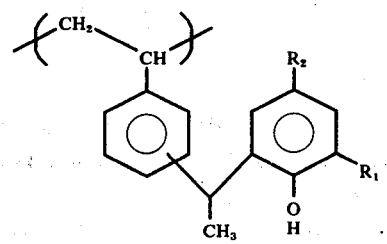

7. The polymer of claim 3, additionally comprising m units of a comonomer, wherein m is from 0.25 to 2.0 times n.

8. The polymer of claim 7 wherein R$_1$ is methyl and R$_2$ is methyl or hydrogen.

9. The polymer of claim 8 wherein the comonomer is hydrolyzed maleic anhydride.

10. The process for preparing the compound

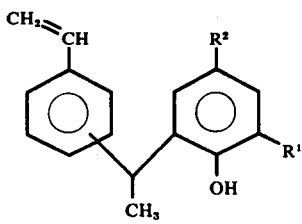

which comprises forming, a mixture of an alkylphenol of the formula

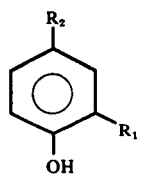

wherein R$_1$ is a saturated lower alkyl of from 1 to 5 carbon atoms and R$_2$ is hydrogen or a saturated lower alkyl of from 1 to 5 carbon atoms, from about 1 to about 5 moles per mole of alkylphenol of divinylbenzene and a catalytically effective amount of a metal phenoxide alkylation catalyst selected from the group consisting of aluminum$^{III}$ phenoxide, zirconium$^{IV}$ phenoxide, hafnium$^{IV}$ phenoxide, tantalum$^{V}$ phenoxide, and gallium$^{III}$ phenoxide; maintaining the mixture at an elevated temperature of from 75° to about 300° C for from 10 minutes to about 20 hours; and thereafter separating the compound of claim 1 from the metal phenoxide alkylation catalyst.

11. The process of claim 10 wherein R$_1$ is methyl and R$_2$ is methyl or hydrogen and the metal phenoxide alkylation catalyst is aluminum$^{III}$ phenoxide.

12. The process for preparing the polymer of claim 3, which comprises contacting not less than $n$ molecules of a styrylphenol of the formula

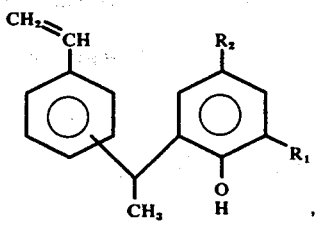

wherein $R_1$ is a lower alkyl of from 1 to 5 carbons inclusive, and $R_2$ is hydrogen or a lower alkyl of from 1 to 5 carbons inclusive with a catalytically effective amount of an acid cationic catalyst at a temperature of from $-100°$ to $50°$ C and thereafter separating the polymer of claim 4 from the catalyst.

13. The process of claim 12 wherein the catalyst is a $BF_3$ catalyst.

14. The process for preparing the polymer of claim 3 which comprises chemically blocking the hydroxyl groups of not less than $n$ molecules of the styrylphenol of the formula

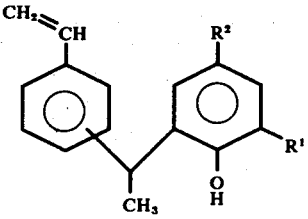

wherein $R_1$ is a lower alkyl of from 1 to 5 carbons inclusive and $R_2$ is hydrogen or a lower alkyl of from 1 to 5 carbons inclusive; polymerizing not less than $n$ molecules of the chemically blocked styrylphenol in the presence of a catalytically effective amount of a free radical initiator at a temperature of from $50°$ to $125°$ C to yield a polymeric product; unblocking and restoring the hydroxyl groups; and recovering the polymer of claim 4.

* * * * *